United States Patent
Iwama

(10) Patent No.: US 10,758,109 B2
(45) Date of Patent: Sep. 1, 2020

(54) MEDICAL EXAMINATION SIGHT MAINTAINING VIDEOSCOPE

(71) Applicant: MPI Inc., Tokyo (JP)

(72) Inventor: Takeshi Iwama, Tokyo (JP)

(73) Assignee: MPI Inc. (JP)

( * ) Notice: Subject to any disclaimer, the term of this patent is extended or adjusted under 35 U.S.C. 154(b) by 33 days.

(21) Appl. No.: 16/260,708

(22) Filed: Jan. 29, 2019

(65) Prior Publication Data

US 2019/0150723 A1 May 23, 2019

Related U.S. Application Data

(63) Continuation of application No. PCT/JP2018/000495, filed on Jan. 11, 2018.

(30) Foreign Application Priority Data

Mar. 10, 2017 (JP) .................. 2017-046207

(51) Int. Cl.
| | |
|---|---|
| *A61B 1/227* | (2006.01) |
| *A61B 1/06* | (2006.01) |
| *A61B 1/00* | (2006.01) |
| *A61B 1/04* | (2006.01) |
| *A61B 1/233* | (2006.01) |
| *A61B 1/24* | (2006.01) |
| *G02B 23/24* | (2006.01) |

(52) U.S. Cl.
CPC ............ *A61B 1/00* (2013.01); *A61B 1/00045* (2013.01); *A61B 1/04* (2013.01); *A61B 1/042* (2013.01); *A61B 1/06* (2013.01); *A61B 1/227* (2013.01); *A61B 1/233* (2013.01); *A61B 1/24* (2013.01); *G02B 23/24* (2013.01); *A61B 1/00066* (2013.01)

(58) Field of Classification Search
CPC ........ A61B 1/227; A61B 1/00; A61B 1/00045
See application file for complete search history.

(56) References Cited

U.S. PATENT DOCUMENTS

| | | | | |
|---|---|---|---|---|
| 5,879,289 A | * | 3/1999 | Yarush ............... | A61B 1/00039 600/109 |
| 2005/0010084 A1 | * | 1/2005 | Tsai ................... | A61B 1/00105 600/200 |
| 2007/0106121 A1 | * | 5/2007 | Yokota ............... | A61B 1/00052 600/188 |
| 2012/0165605 A1 | * | 6/2012 | Yamazaki .......... | G02B 23/2476 600/106 |

(Continued)

FOREIGN PATENT DOCUMENTS

| | | |
|---|---|---|
| CN | 102711584 A | 10/2012 |
| EP | 2502548 A1 | 9/2012 |

(Continued)

*Primary Examiner* — Christian A Sevilla
(74) *Attorney, Agent, or Firm* — Harness, Dickey & Pierce, P.L.C.

(57) ABSTRACT

In a medical examination sight maintaining videoscope of the present invention, in a state where an examination attachment is attached, it becomes possible to position a scope tip-end section and an object to be examined in a positional relationship in which the scope tip-end section and the object to be examined are straightly aligned with a line of sight of the user. At this time, a monitor is situated at such a position that the user can look straight at the monitor and the line of sight of the user is avoided.

1 Claim, 5 Drawing Sheets

(56) References Cited

U.S. PATENT DOCUMENTS

2013/0128223 A1    5/2013    Wood et al.
2013/0237754 A1*    9/2013    Berglund ............. A61B 5/0073
                                                                                                   600/109

FOREIGN PATENT DOCUMENTS

| JP | 2005-519666 A | 7/2005 |
| WO | WO-02/025756 A2 | 7/2002 |
| WO | WO-2012/017810 A1 | 2/2012 |
| WO | WO-2013/071153 A1 | 5/2013 |
| WO | WO-2013/138081 A1 | 9/2013 |

* cited by examiner

MEDICAL EXAMINATION SIGHT MAINTAINING VIDEOSCOPE

CROSS-REFERENCE TO RELATED APPLICATIONS

This application is a Continuation Application of PCT Application No. PCT/JP2018/000495, filed Jan. 11, 2018 and based upon and claiming the benefit of priority from prior Japanese Patent Application No. 2017-046207, filed Mar. 10, 2017, the entire contents of all of which are incorporated herein by reference.

BACKGROUND OF THE INVENTION

1. Field of the Invention

The present invention relates to a technique making it possible to shoot and record an object to be examined and visualize the object to be examined on a monitor while maintaining the object to be examined, for example, an aural cavity, oral cavity, nasal cavity or the like within a range (i.e., sight) in which the object can actually be viewed.

2. Description of the Related Art

A videoscope is known as a tool configured to optically observe an object to be examined such as an aural cavity, oral cavity, nasal cavity or the like (as in Patent Literature 1 (JP 2005-519666 A)). In the videoscope, for example, a user inserts a scope tip-end section into an object to be examined or operates the scope tip-end section along the object to be examined. At this time, a diagnosis (medical examination, treatment) is carried out while the object to be examined visualized on a monitor is being viewed.

BRIEF SUMMARY OF THE INVENTION

It is desired that the insertability and operability of the scope tip-end section be improved with respect to the object to be examined at the time of diagnosis (medical examination, treatment). However, with the existing videoscope, it is not possible to maintain the object to be examined within the sight of the user (i.e., the line of sight of the user) because of the arrangement structure of the monitor. For this reason, there has been a certain limitation on the improvement in the insertability and operability of the scope tip-end section with respect to the object to be examined.

An embodiment described herein aims to provide a technique making it possible to image and record an object to be examined and visualize the object on a monitor while maintaining the object to be examined, for example, an aural cavity, oral cavity, nasal cavity or the like within the sight to thereby improve the insertability and operability of the scope tip-end section with respect to the object to be examined.

In order to achieve such an object, by virtue of the medical examination sight maintaining videoscope of the present invention, in a state where an examination attachment is attached, it becomes possible to position a scope tip-end section and object to examined in a positional relationship in which the scope tip-end section and object to be examined are straightly aligned with the line of sight of the user. At this time, a monitor is situated at a position avoiding the line of sight of the user.

According to the present invention, it is made possible to image and record an object to be examined and visualize the object on a monitor while maintaining the object to be examined, for example, an aural cavity, oral cavity, nasal cavity or the like within the sight, whereby it is possible to improve the insertability and operability of the scope tip-end section with respect to the object to be examined.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

One of the embodiments of the present invention will be described hereinafter with reference to the accompanying drawings.

"Outline of Medical Examination Sight Maintaining Videoscope 1"

Figure 1:
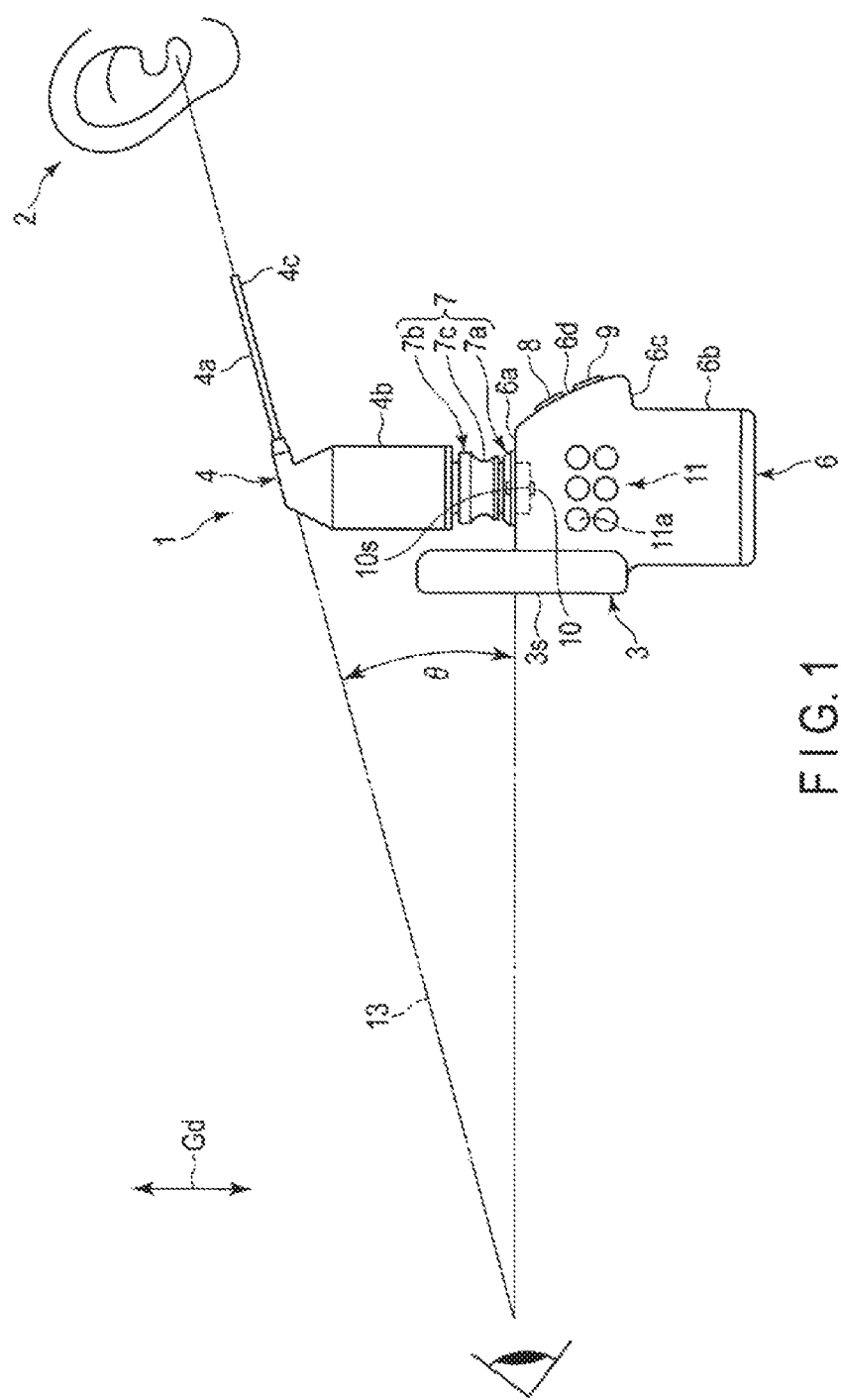
FIG. 1 is a view schematically showing the specification of a medical examination sight maintaining videoscope according to an embodiment of the present invention.
Figure 2:
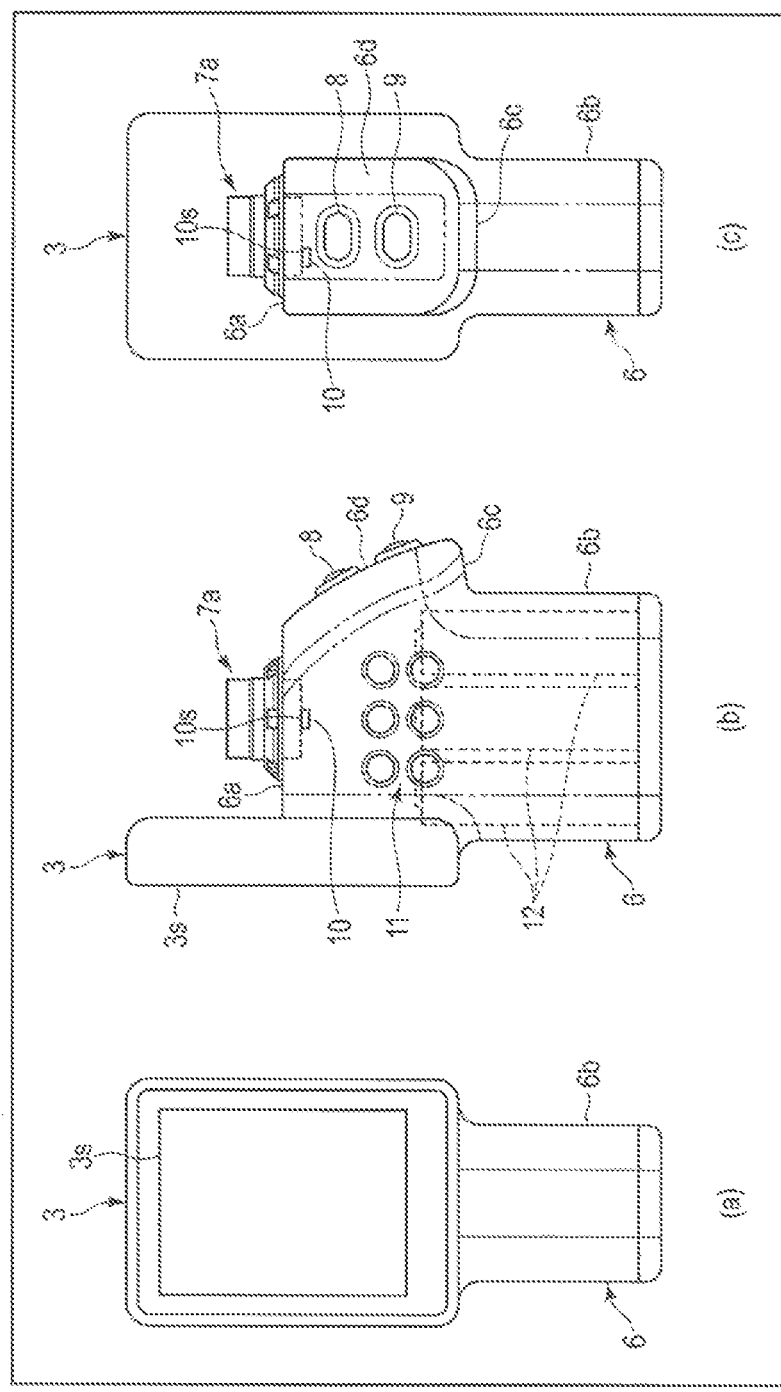
FIG. 2 (*a*) is a plan view of a scope main body viewed from the monitor side, FIG. 2 (*b*) is a side view of the scope main body, and FIG. 2 (*c*) is a plan view of the scope main body viewed from the operation section side.

As shown in FIG. 1, a medical examination sight maintaining videoscope 1 of this embodiment makes it possible to shoot and record an object to be examined 2 and visualize the object to be examined 2 on a monitor 3 (display surface 3*s*) while maintaining the object to be examined 2 within the sight. Here, as the object to be examined 2, various cavities of a human body such as an aural cavity, oral cavity, nasal cavity, and the like can be assumed. The videoscope 1 includes a plurality of types of dedicated examination attachments 4 and 5 (see FIG. 5 and FIG. 6) configured to examine these cavities.

Figure 5:
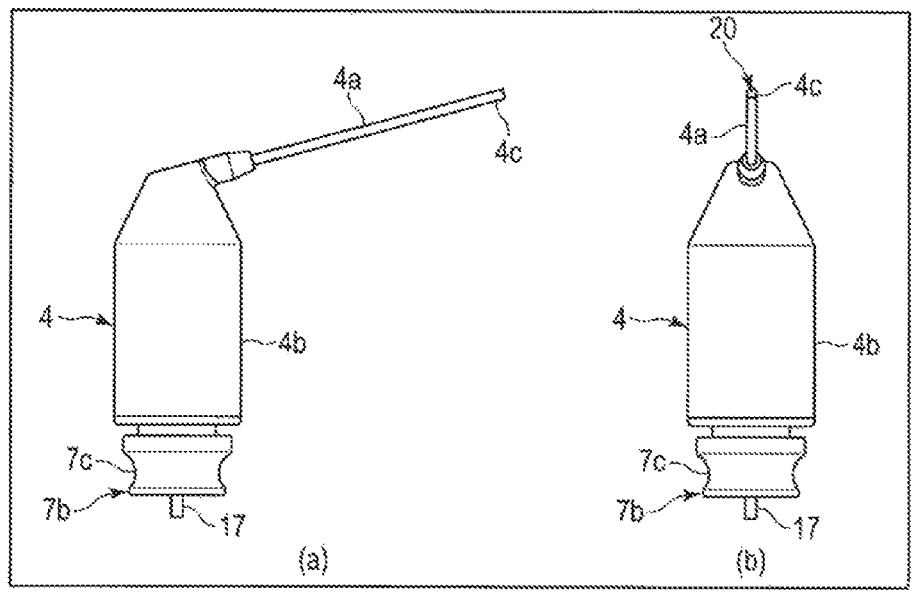
FIG. 5 (*a*) is a side view of an aural cavity examination attachment, and FIG. 5 (*b*) is a front view of the aural cavity examination attachment.
Figure 6:
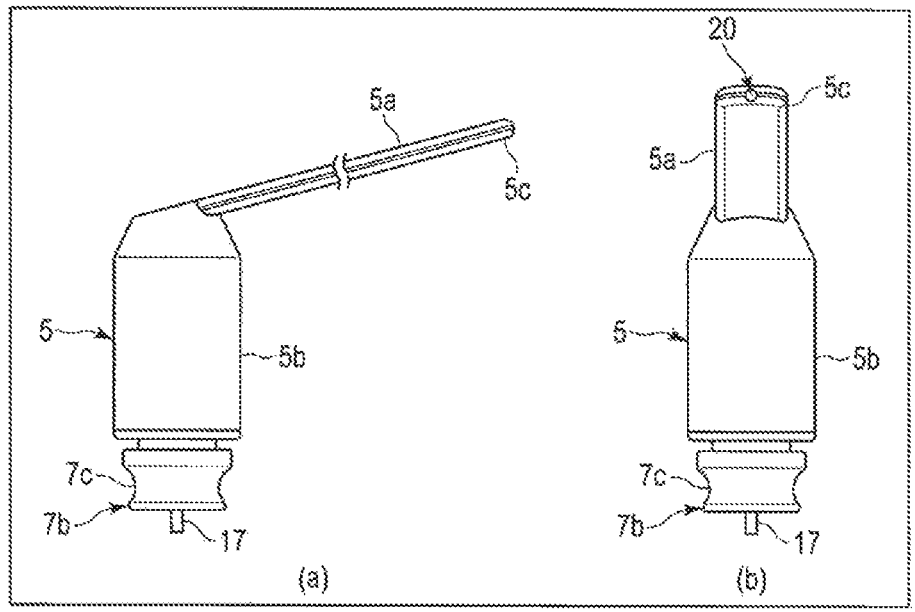
FIG. 6 (*a*) is a side view of an oral cavity examination attachment, and FIG. 6 (*b*) is a front view of the oral cavity examination attachment.
Figure 7:
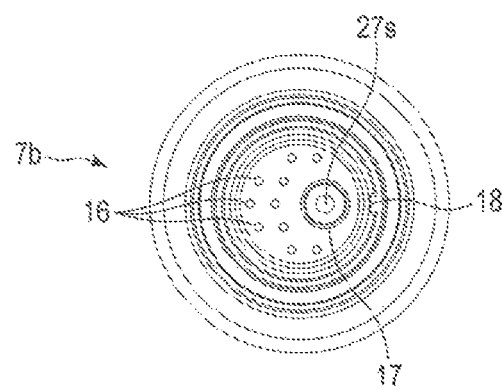
FIG. 7 is a plan view of a connector section of an examination attachment.

As one example, in FIG. 5, an aural cavity examination attachment 4 is shown. The aural cavity examination attachment 4 is provided with an aural cavity insertion section 4*a* which can be inserted into an earhole. The aural cavity insertion section 4a has a cylindrical shape and extends straight. In FIG. 6, an oral cavity examination attachment 5 is shown. The oral cavity examination attachment 5 is provided with an oral cavity insertion section 5a which can be inserted into the inside of a mouth while pressing a tongue. The oral cavity insertion section 5a has a flat shape and extends straight.

Each of the insertion sections 4a and 5a is supported on each of support sections 4b and 5b having a common shape. Each of the support sections 4b and 5b is configured in the vertical direction in terms of the direction of gravitational force Gd (see FIG. 1). Each of the insertion sections 4a and 5a is supported on an upper end of each of the support sections 4b and 5b. To a lower end of each of the support sections 4b and 5b, a second connector section 7b of an attaching mechanism (connector 7) is attached.

Furthermore, each of the insertion sections 4a and 5a (examination attachments 4 and 5) is provided with each of scope tip-end sections 4c and 5c. Each of the scope tip-end sections 4c and 5c is configured to be able to be inserted into the object to be examined 2 or to be operated along the object to be examined 2. Each of the scope tip-end sections 4c and 5c is provided with an imaging unit 20 to be described later. An image of the object to be examined 2 is captured in a scope main body 6 to be described later through the imaging unit 20, and is used for shooting, recording, and visualization. Details of the imaging unit 20 will be described later.

It should be noted that the inclination angle of each of the insertion sections 4a and 5a (scope tip-end sections 4c and 5c) is set by assuming a state where each of the examination attachments 4 and 5 is attached to the scope main body 6. For example, in FIG. 1, the aural cavity examination attachment 4 is attached to the scope main body 6 (attaching section 6a (uppermost surface)). In this case, the inclination angle θ is specified as an angle which each of the insertion sections 4a and 5a (scope tip-end sections 4c and 5c) forms with the attaching section 6a (uppermost surface). As one example, the inclination angle θ is set within a range of acute angles)(0°<θ<90°, desirably within a range of 10°<θ<30° and, more desirably, is set to 15° or is set to an angle in the neighborhood of 15°.

As shown in FIG. 1 through FIG. 4, the medical examination sight maintaining videoscope 1 includes a scope main body 6 provided with a function of shooting, recording, and visualizing the object to be examined 2. A plurality of types of examination attachments 4 and 5 can selectively be attached to the scope main body 6 according to the type of the object to be examined 2. For example, when the aural cavity is made the object to be examined 2, an aural cavity examination attachment 4 is attached to the scope main body 6. Subsequently, when the oral cavity is made the object to be examined 2, the currently attached aural cavity examination attachment 4 is detached from the scope main body 6 and, thereafter an oral cavity examination attachment 5 is attached to the scope main body 6.

Accordingly, the scope main body 6 is provided with an attaching section 6a to which a plurality of types of examination attachments 4 and 5 can selectively be attached. The attaching section 6a is configured on the uppermost surface of the scope main body 6 in terms of the direction of gravitational force Gd. To the attaching section 6a (uppermost surface), the examination attachments 4 and 5 are selectively attached through an attaching mechanism.

As one example of the attaching mechanism, a connector 7 (first connector section 7a, second connector section 7b) to be described later is applied. The first connector section 7a is attached to the attaching section 6a (uppermost surface) of the scope main body 6. The second connector section 7b is attached to the examination attachments 4 and 5 (lower end of the support sections 4b and 5b).

In such a configuration, both the connector sections 7a and 7b are coupled to each other. Thereby, the examination attachments 4 and 5 can selectively be attached to the scope main body 6. Thus, it is possible to optically, electrically, and mechanistically couple the imaging unit 20 to be described later and scope main body 6 to each other. It should be noted that details of the first connector section 7a and second connector section 7b will be described later.

Furthermore, the scope main body 6 is provided with a grip section 6b which can be gripped with fingers of the user and slip-stop section 6c. The grip section 6b is configured at a lower part of the scope main body 6 in terms of the direction of gravitational force Gd, in other words, the grip section 6b is configured directly below the attaching section 6a. The grip section 6b has an extended elliptical contour which the user can grip with his or her one hand (right hand, left hand). The slip-stop section 6c is provided at a part adjacent to the upper part of the grip section 6b in terms of the direction of gravitational force Gd. The slip-stop section 6c is configured in such a manner as to bulge out of the grip section 6b.

In such a configuration, the user grips the grip section 6b with his or her fingers. At this time, part of the fingers of the user (for example, index finger and middle finger) are caught on the slip-stop section 6c. Thereby, the grip section 6b never slips off the fingers of the user downwardly in terms of the direction of gravitational force.

Furthermore, the scope main body 6 is provided with an operation section 6d on which a shooting button 8 and recording button 9 are provided. The shooting button 8 and recording button 9 are arranged vertically in line in terms of the direction of gravitational force Gd. The operation section 6d is positioned between the attaching section 6a (uppermost surface) and grip section 6b. In other words, the operation section 6d is configured in such a manner as to be downwardly continuous from the attaching section 6a (uppermost surface) in the direction of gravitational force Gd. The operation section 6d has a contour along a trajectory of fingertips (i.e., range of movement) in a state where the user grips the grip section 6b with his or her fingers. The operation section has a contour of a curved surface shape smooth in vertical direction in terms of the direction of gravitational force Gd.

In such a configuration, the user grips the grip section 6b with his or her fingers. At this time, the operation section 6d is positioned within the range of movement of the fingers (for example, index finger and middle finger) of the user. Thereby, the user can move the fingers smoothly and easily along the operation section 6d. Thus, the user can smoothly and easily press the shooting button 8 and recording button 9.

Furthermore, the scope main body 6 is provided with a light source 10 and the aforementioned monitor 3. The monitor 3 is configured in such a manner as to be able to visualize the object to be examined 2 on the display surface 3s thereof. The monitor 3 is positioned on the opposite side of the operation section 6d. The display surface 3s of the monitor 3 is positioned in such a manner as to face in a direction opposite to the operation section 6d (operation surface provided with the shooting button 8 and recording button 9). The monitor 3 is positioned in such a manner as to be downwardly shifted from the attaching section 6a (uppermost surface) in terms of the direction of gravitational force Gd.

In such a configuration, the user grips the grip section 6b with his or her fingers. At this time, the monitor 3 (display surface 3s) is positioned in such a manner that the user can look straight at the monitor 3. It should be noted that the light source 10 is arranged in the first connector section 7a to be described later for the purpose of illuminating the object to be examined 2. As the light source 10, an existing light-emitting element (LED) can be applied. The arrangement of the light source 10 will be described later.

Further, the scope main body 6 is provided with a button group 11 including a power button 11a (see FIG. 1), menu button, and the like. For example, by pressing the power button 11a, it becomes possible to exert the function of shooting, recording, and visualizing the object to be examined 2. As the power source, for example, three primary cells 12 (AA cells) are applied (see FIG. 2 (b)). It should be noticed that the button group 11 is arranged at such a position that the button group 11 cannot be pressed by mistake in a state where the grip section 6b is gripped by the user with his or her fingers. In the drawing, as one example, the button group 11 is arranged on the side surface of the scope main body 6 between the operation section 6d and monitor 3.

"Effective Advantage of Medical Examination Sight Maintaining Videoscope 1"

As shown in FIG. 1, the aural cavity examination attachment 4 is attached to the scope main body 6 (attaching section 6a) through, for example, the connector 7 (first connector section 7a, second connector section 7b) to be described later. At this time, the support section 4b of the examination attachment 4 is positioned in such a manner as to exceed the uppermost end of the monitor 3 in terms of the direction of gravitational force Gd. On the other hand, when the power button 11a is pressed, the function of shooting, recording, and visualizing the object to be examined is exerted. Subsequently, the grip section 6b is gripped with the fingers of the user. In this state, the grip section 6b never slips off the fingers of the user by virtue of the slip-stop section 6c.

Next, in the state where the user grips the grip section 6b with his or her fingers, the user inserts the aural cavity insertion section 4a (for example, the scope tip-end section 4c) into the aural cavity which is the object to be examined 2 or operates the aural cavity insertion section 4a along the inside of the aural cavity. At this time, it becomes possible to position the aural cavity insertion section 4a (scope tip-end section 4c) and object to be examined 2 (aural cavity) in a positional relationship in which the aural cavity insertion section 4a and object to be examined 2 are straightly aligned with the line of sight 13 of the user. Thus, the monitor 3 is situated at such a position that the user can look straight at the monitor 3 and the line of sight 13 of the user is avoided.

According to the videoscope 1, the monitor 3 can be situated at a position avoiding the line of sight 13 of the user at the time of medical examination. Thereby, it is possible to maintain the object to be examined 2 (for example, the aural cavity) within the sight of the user (i.e., the line of sight 13 of the user). At the same time, it becomes possible to shoot and record the object to be examined, and visualize the object to be examined 2 on the monitor 3 (display surface 3s). As a result, it is possible to remarkably improve the insertability and operability of the scope tip-end sections 4c and 5c with respect to the object to be examined 2.

According to the videoscope 1, three primary cells (AA cells) can be applied. Thereby, it is possible to shoot and record the object to be examined 2 and visualize the object to be examined 2 on the monitor 3 (display surface 3s) even in such an environment that an external power source cannot be secured.

According to the videoscope 1, the videoscope 1 is configured in such a manner that the grip section 6b has an extended elliptical shape, and the user can grip the grip section 6b with his or her one hand (right hand, left hand). Thereby, it is possible to prevent the grip section 6b from being rotated inside the fingers of the user. As a result, it is possible to stabilize the insertion direction and operation direction of the scope tip-end sections 4c and 5c with respect to the object to be examined 2.

"About Connector 7"

As shown in FIG. 1 through FIG. 7, the connector 7 includes the circular first connector section 7a, circular second connector section 7b, and release knob 7c. The first connector section 7a and second connector section 7b can be coupled to each other in such a manner as to be concentrically opposed to each other. It should be noted that in a state where both the connector sections 7a and 7b are coupled to each other, the release knob 7c (see FIG. 1 and FIG. 5 through FIG. 7) of the second connector section 7b is drawn toward, for example, the support sections 4b and 5b. At this time, the coupled state of both the connector sections 7a and 7b is released. Thus, the examination attachments 4 and 5 can be detached from the scope main body 6 (attaching section 6a).

Figure 3:
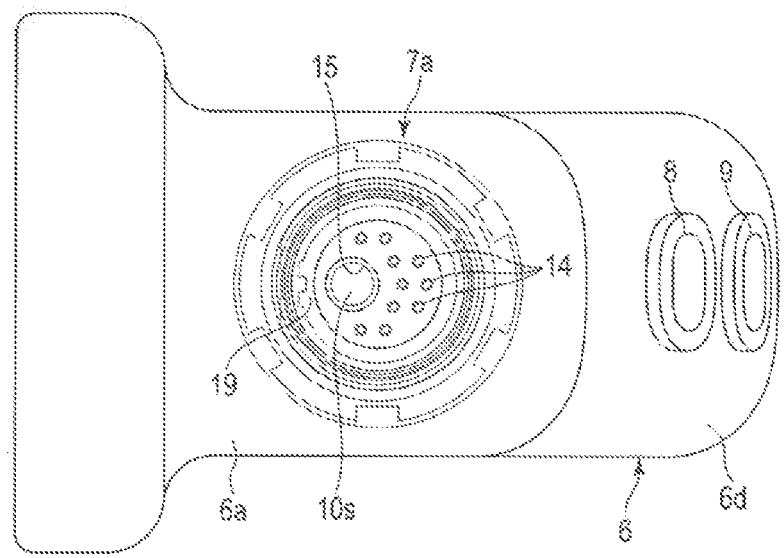
FIG. 3 is a plan view of a connector section of the scope main body.
Figure 4:
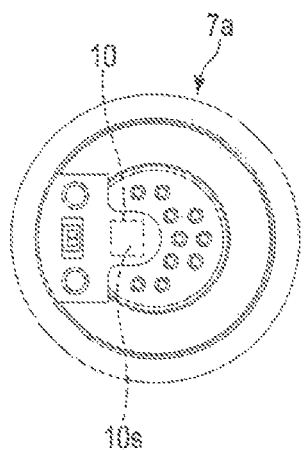
FIG. 4 is a plan view showing the arrangement of a light source incorporated in the scope main body.

Here, the first connector section 7a is provided with a plurality of female terminals 14, insertion pathway 15, and the aforementioned light source 10 (see FIG. 3 and FIG. 4). It should be noted that in FIG. 3, the front side (surface to which the second connector section 7b is coupled) of the first connector section 7a is shown. In FIG. 4, the backside of the first connector section 7a is shown. On the other hand, the second connector section 7b is provided with a plurality of male terminals 16 and hollow holder 17 (see FIG. 5 through FIG. 7).

The hollow holder 17 has both ends (one end and the other end), and is configured in such a manner as to penetrate the second connector section 7b. The hollow holder 17 is configured in such a manner as to be able to be inserted into the insertion pathway 15. The hollow holder 17 is configured in such a manner as to be able to hold therein a light guide 27 (for example, optical fibers 27f) extending from the imaging unit 20 to be described later.

In such a configuration, the light guide 27 is inserted into the hollow holder 17 from the one end thereof to the other end thereof. Thereby, the light guide 27 is held inside the hollow holder 17. In this state, a light incidence plane 27s (see FIG. 7) on which light can be incident is configured in the light guide 27 at the other end (i.e., the part of the light guide exposed from the hollow holder 17) of the hollow holder 17. That is, in the state where the hollow holder 17 is made to hold the light guide 27 therein, the light incidence plane 27s of the light guide 27 is exposed at the other end of the hollow holder 17.

The light source 10 is provided with a light outgoing plane 10s from which light can be emitted toward the light incidence plane 27s of the light guide 27. The light source 10 (light outgoing plane 10s) is positioned in such a manner as to be opposed to the insertion pathway 15 (see FIG. 3). The light source 10 (light outgoing plane 10s) is provided at a position deviated from the center (i.e., center of the circle) of the circular first connector section 7a.

For this reason, the insertion pathway 15 is also provided at a position deviated from the center (i.e., center of the circle) of the circular first connector section 7a. Thus, the hollow holder 17 is also provided at a position deviated from the center (i.e., center of the circle) of the circular second connector section 7b correspondingly to the eccentric position of the insertion pathway 15 and light source 10 (light outgoing plane 10s).

As described above, according to the connector 7, for example, the second connector section 7b is pressed into, for example, the first connector section 7a. At this time, a convex guide 19 (see FIG. 3) is inserted along a concave guide 18 (see FIG. 7). Thereby, the male terminals 16 and female terminals 14 are electrically coupled to each other. At the time of such electrical coupling, the hollow holder 17 is inserted into the insertion pathway 15. The light incidence plane 27s of the light guide 27 (optical fibers 27f) and light outgoing plane 10s of the light source 10 are arranged in such a manner as to be opposed to each other. At this time, the light guide 27 (optical fibers 27f) and light source 10 are optically coupled to each other. Thus, the imaging unit 20 and scope main body 6 are optically, electrically, and mechanistically coupled to each other.

"About Imaging Unit 20"

Figure 8:
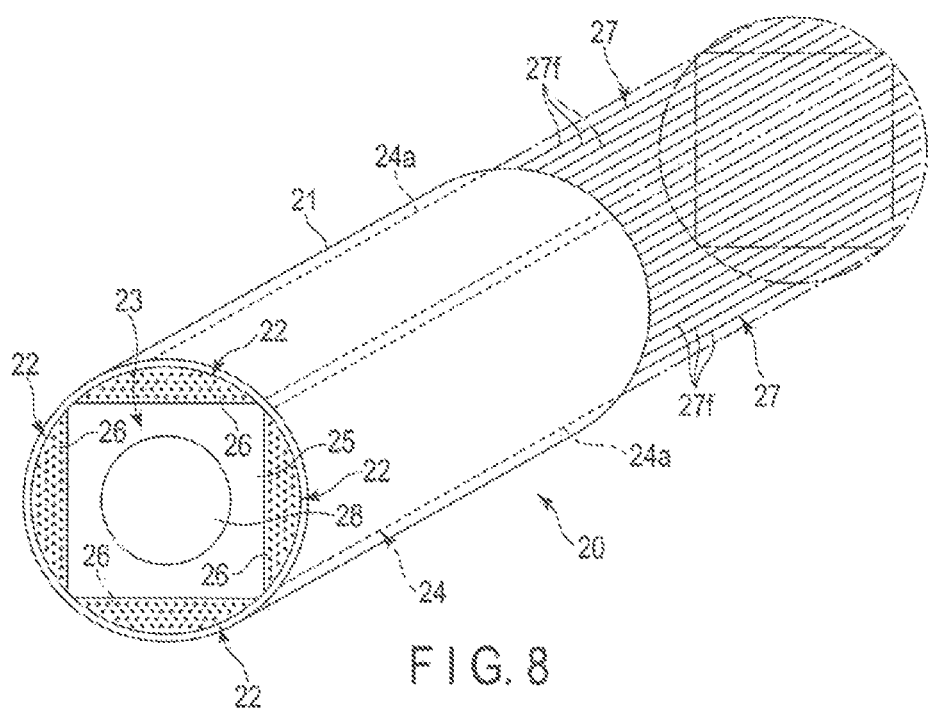
FIG. 8 is a perspective view showing the configuration of a scope tip-end section of the examination attachment.

As shown in FIG. 8, the imaging unit 20 is configured in such a manner as to enable the external dimension of the scope tip-end sections 4c and 5c to be set to, for example, an ultra-fine diameter less than several millimeters. The imaging unit 20 includes a hollow cylindrical case main body 21 which can be arranged inside the scope tip-end sections 4c and 5c, a plurality of light emitting sections 22, and light receiving section 23. The light emitting sections 22 and light receiving section 23 are accommodated in the case main body 21. The light emitting sections 22 are configured to be able to emit light toward the object to be examined 2. The light receiving section 23 is configured in such a manner that an image from the object to be examined 2 illuminated with light can be input thereto. Inside the case main body 21, the light emitting sections 22 are laid out along the circumference of the light receiving section 23.

Furthermore, the imaging unit 20 includes a hollow regular quadrangular prismatic holder 24. The holder 24 is configured to be able to hold the light emitting sections 22 and light receiving section 23 inside the case main body 21. The holder 24 is provided with four wall sections 24a opposed in parallel to each other in such a manner that the inside of the case main body 21 is partitioned into parts. Regarding the four wall sections 24a, wall sections 24a adjacent to each other are perpendicular to each other.

Here, in the state where the holder 24 is accommodated in the case main body 21, the inside of the case main body 21 is partitioned into a first region 25 and second regions 26. The second regions 26 are laid out along the circumference of the first region 25. The first region 25 has a square cross-sectional contour surrounded with the four wall sections 24a. The second regions 26 have a cross-sectional contour surrounded with the wall sections 24a and case main body 21. The light receiving section 23 is accommodated in the first region 25. The light emitting sections 22 are accommodated in the second regions 26.

The light emitting sections 22 are configured to be able to emit light toward the object to be examined 2. To the light emitting sections 22, the light guide 27 having both ends, and aforementioned light source 10 are connected. The one end section of the light guide 27 is accommodated in the case main body 21 of the imaging unit 20. The other end section of the light guide 27 is configured in such a manner that light from the light source 10 can be incident thereon in the state where the other end section of the light guide 27 is held inside the hollow holder 17.

The light receiving section 23 is configured in such a manner that an image from the object to be examined 2 illuminated with light can be input thereto. The light receiving section 23 is provided with an objective lens 28 and sensor (not shown). The sensor is arranged behind the objective lens 28. The objective lens 28 is fixed to the holder 24. As the sensor, for example, an imaging element such as a CMOS, CCD, and the like can be applied. The sensor is fixed to the holder 24 by means of a fastening device (not shown).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical examination sight maintaining videoscope making it possible to shoot and record an object to be examined and visualize the object to be examined on a monitor while maintaining the object to be examined within a sight, said videoscope comprising:
  a plurality of types of examination attachments;
  a scope main body to which the plurality of types of examination attachments are selectively attached; and
  a scope tip-end section to be provided on each of the examination attachments, and can be inserted into the object to be examined or can be operated along the object to be examined, wherein
  the scope main body includes:
  an attaching section to which the plurality of types of examination attachments can selectively be attached,
  a light source configured to illuminate the object to be examined,
  an operation section provided with buttons configured to shoot and record the object to be examined,
  a monitor including a display surface configured to visualize the object to be examined thereon, and
  a grip section which can be gripped with fingers of the user,
  in a state where the user grips the grip section with his or her fingers, the operation section includes a contour along a trajectory of fingertips, and the monitor is positioned in such a manner that the user can look straight at the monitor,
  a part of the grip section on the upper side thereof in the direction of gravitational force is configured in such a manner as to bulge out of the grip section so that the grip section gripped by the user with his or her fingers does not slip off the fingers downwardly in the direction of gravitational force,
  the monitor is positioned on the opposite side of the operation section, and the display surface of the monitor is positioned in such a manner as to face in a direction opposite to the operation section,
  the scope tip-end section is positioned on the opposite side of the monitor, and is positioned on the upper side of the monitor and the operation section in terms of the direction of gravitational force,
  the scope tip-end section is positioned in such a manner as to face in a direction opposite to the display surface of the monitor, and in a state where the selected examination attachment is attached to the attaching section, it becomes possible to position the scope tip-end section and the object to be examined in a positional relationship in which the scope tip-end section and the object to be examined are straightly aligned with the line of sight of the user and, at this time, the monitor is situated at a position avoiding the line of sight of the user.

* * * * *